US010699595B2

(12) United States Patent
Flores et al.

(10) Patent No.: US 10,699,595 B2
(45) Date of Patent: Jun. 30, 2020

(54) MONITORING AND STATUS DETECTION FOR CONSUMABLE ITEMS

(71) Applicant: International Business Machines Corporation, Armonk, NY (US)

(72) Inventors: Christina I. Flores, Keller, TX (US); Romelia H. Flores, Keller, TX (US); Erik H. Katzen, Argyle, TX (US); Sumit Patel, Irving, TX (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 964 days.

(21) Appl. No.: 14/821,205

(22) Filed: Aug. 7, 2015

(65) Prior Publication Data
US 2017/0039885 A1 Feb. 9, 2017

(51) Int. Cl.
G09B 19/00 (2006.01)
G16H 20/60 (2018.01)
G16H 20/30 (2018.01)
G16H 20/40 (2018.01)

(52) U.S. Cl.
CPC ......... G09B 19/0092 (2013.01); G16H 20/30 (2018.01); G16H 20/40 (2018.01); G16H 20/60 (2018.01)

(58) Field of Classification Search
CPC .... G09B 19/0092; G16H 20/30; G16H 20/40; G16H 20/60; G16H 20/70; G16H 20/90
See application file for complete search history.

(56) References Cited

U.S. PATENT DOCUMENTS

| 5,263,491 A * | 11/1993 | Thornton ................. A61B 5/22 600/483 |
| 7,328,671 B2 * | 2/2008 | Kates ...................... A01K 15/02 119/719 |
| 7,483,964 B1 | 1/2009 | Jackson et al. |
| 7,565,225 B2 | 7/2009 | Dushane |
| 8,690,578 B1 | 4/2014 | Nusbaum et al. |
| 9,131,266 B2 | 9/2015 | Guedalia et al. |

(Continued)

FOREIGN PATENT DOCUMENTS

CN 103377397 A1 10/2013
CN 107683491 A 2/2018
(Continued)

OTHER PUBLICATIONS

IBM: List of IBM Patents or Patent Applications Treated as Related, Jan. 13, 2016, 2 pg.
(Continued)

Primary Examiner — Robert J Utama
(74) Attorney, Agent, or Firm — Cuenot, Forsythe & Kim, LLC

(57) ABSTRACT

Monitoring oral intake of consumable items may include aggregating, using a processor, oral intake information for a user from a plurality of devices belonging to a same device domain of the user in real time and comparing, using the processor, the oral intake information with a user profile of the user. An instruction for a selected device of the plurality of devices may be generated, using the processor, according to the comparing. The instruction may be sent to the selected device, using the processor. The selected device may execute the instruction.

18 Claims, 8 Drawing Sheets

(56) References Cited

U.S. PATENT DOCUMENTS

| | | | |
|---|---|---|---|
| 9,146,147 B1* | 9/2015 | Bakhsh | A47G 21/02 |
| 9,168,000 B2* | 10/2015 | Dunki-Jacobs | A61B 5/4839 |
| 9,189,021 B2* | 11/2015 | Jerauld | G06F 1/163 |
| 9,436,771 B1* | 9/2016 | Caragol | G06F 16/9554 |
| 9,456,787 B2* | 10/2016 | Venkatraman | A61B 5/721 |
| 9,621,433 B2 | 4/2017 | Yoshida et al. | |
| 9,716,703 B2 | 7/2017 | Entezari | |
| 9,774,507 B2 | 9/2017 | Britt | |
| 10,006,896 B2* | 6/2018 | Fernstrom | G01N 33/02 |
| 10,130,277 B2* | 11/2018 | Connor | A61B 5/7285 |
| 10,135,777 B2 | 11/2018 | Flores | |
| 2001/0049470 A1* | 12/2001 | Mault | A61B 5/02055 600/300 |
| 2003/0009202 A1* | 1/2003 | Levine | A61B 5/0031 607/58 |
| 2003/0065257 A1* | 4/2003 | Mault | A61B 5/02055 600/407 |
| 2004/0147816 A1* | 7/2004 | Policker | A61B 5/04884 600/300 |
| 2009/0198506 A1* | 8/2009 | Gupta | G06F 17/30702 705/1.1 |
| 2012/0009550 A1* | 1/2012 | Gayle | G09B 19/0092 434/127 |
| 2012/0072302 A1* | 3/2012 | Chen | G06Q 30/0631 705/26.7 |
| 2012/0101874 A1* | 4/2012 | Ben-Haim | A61B 5/0031 705/14.1 |
| 2012/0179665 A1* | 7/2012 | Baarman | G06F 19/3475 707/709 |
| 2012/0317167 A1* | 12/2012 | Rahman | A61B 5/1118 709/202 |
| 2013/0004923 A1* | 1/2013 | Utter, II | G06F 19/3475 434/127 |
| 2013/0035871 A1* | 2/2013 | Mayou | A61B 5/14532 702/26 |
| 2013/0038510 A1* | 2/2013 | Brin | G02B 27/017 345/8 |
| 2013/0105565 A1* | 5/2013 | Kamprath | G06F 19/3475 235/375 |
| 2013/0267794 A1 | 10/2013 | Fernstrom et al. | |
| 2013/0273506 A1* | 10/2013 | Melowsky | G09B 19/0092 434/127 |
| 2014/0064232 A1 | 3/2014 | Chang et al. | |
| 2014/0147829 A1* | 5/2014 | Jerauld | G06F 1/163 434/430 |
| 2014/0241373 A1 | 8/2014 | Pasam et al. | |
| 2014/0242983 A1 | 8/2014 | Chang et al. | |
| 2014/0244001 A1* | 8/2014 | Glickfield | H04L 67/16 700/33 |
| 2014/0256324 A1 | 9/2014 | Mohanty et al. | |
| 2014/0267299 A1* | 9/2014 | Couse | G06T 11/206 345/440.2 |
| 2014/0279341 A1* | 9/2014 | Bhardwaj | A61B 5/686 705/37 |
| 2014/0315162 A1* | 10/2014 | Ehrenkranz | G01G 19/4146 434/127 |
| 2014/0335490 A1* | 11/2014 | Baarman | A61B 5/002 434/236 |
| 2014/0349257 A1* | 11/2014 | Connor | G09B 19/0092 434/127 |
| 2015/0006695 A1 | 1/2015 | Gupta | |
| 2015/0019342 A1* | 1/2015 | Gupta | G06Q 30/0269 705/14.66 |
| 2015/0080672 A1* | 3/2015 | Biswas | A61B 5/6831 600/301 |
| 2015/0088979 A1* | 3/2015 | Dong | H04L 67/10 709/203 |
| 2015/0095790 A1 | 4/2015 | Yoshida et al. | |
| 2015/0118658 A1* | 4/2015 | Mayou | A61B 5/14552 434/127 |
| 2015/0132722 A1* | 5/2015 | Menczel | A61B 5/01 434/127 |
| 2015/0140539 A1* | 5/2015 | Zamierowski | G09B 23/303 434/268 |
| 2015/0160363 A1* | 6/2015 | Hornbostel | G01V 3/083 324/337 |
| 2016/0006815 A1 | 1/2016 | Dong et al. | |
| 2016/0105402 A1 | 4/2016 | Soon-Shiong | |
| 2016/0171339 A1* | 6/2016 | Choi | G06K 9/6293 382/103 |
| 2016/0180679 A1* | 6/2016 | Cowley | G08B 21/02 340/573.1 |
| 2016/0180723 A1* | 6/2016 | Tatourian | G09B 5/00 434/237 |
| 2016/0182528 A1 | 6/2016 | Entezari | |
| 2016/0224750 A1* | 8/2016 | Kethman | G06F 19/00 |
| 2016/0301707 A1 | 10/2016 | Cheng et al. | |
| 2016/0308861 A1 | 10/2016 | Ameling et al. | |
| 2016/0323767 A1 | 11/2016 | Abdullah et al. | |
| 2016/0328991 A1* | 11/2016 | Simpson | A61B 5/742 |
| 2016/0350514 A1* | 12/2016 | Rajendran | G06Q 10/10 |
| 2016/0352673 A1 | 12/2016 | Flores | |
| 2016/0366853 A1* | 12/2016 | Mainini | A01K 11/008 |
| 2017/0006135 A1 | 1/2017 | Siebel | |
| 2017/0006595 A1* | 1/2017 | Zakaria | H04L 67/12 |
| 2017/0018001 A1* | 1/2017 | Tunnell | G06Q 30/0255 |
| 2017/0024535 A1* | 1/2017 | Matz | G06F 19/3418 |
| 2017/0039885 A1* | 2/2017 | Flores | G09B 19/0092 |
| 2017/0103677 A1* | 4/2017 | Bhattacharjee | G09B 5/02 |
| 2017/0178534 A1* | 6/2017 | Prakash | G09B 19/0092 |
| 2017/0220751 A1* | 8/2017 | Davis | A61B 5/0015 |
| 2017/0244770 A1 | 8/2017 | Eckerdal et al. | |
| 2018/0088098 A1* | 3/2018 | Mandava | G06Q 10/0833 |
| 2018/0343238 A1 | 11/2018 | Tola | |
| 2019/0052593 A1 | 2/2019 | Flores | |
| 2019/0079474 A1* | 3/2019 | Fadell | G05B 15/02 |

FOREIGN PATENT DOCUMENTS

| | | |
|---|---|---|
| DE | 112016001336 T5 | 12/2017 |
| EP | 2680210 A1 | 1/2014 |
| JP | 2002325288 A | 11/2002 |
| JP | 2003271635 A | 9/2003 |
| JP | 2011160382 A | 8/2011 |
| JP | 2014103304 A | 6/2014 |
| JP | 2018523183 A | 8/2018 |
| WO | 2014193950 A1 | 12/2014 |
| WO | 2015042379 A1 | 3/2015 |
| WO | 2015073722 A1 | 5/2015 |
| WO | 2014103304 A1 | 1/2017 |

OTHER PUBLICATIONS

Flores, C.I. et al., "Leveraging an Internet of Things to Initiate a Physical Object to Perform a Specific Act That Enhances an Interaction of a User With the Physical Object", U.S. Appl. No. 14/722,833, filed May 27, 2015, 52 pages.

Siddique, A., "Google Glass Features; How Medical Uses Will Revolutionize Your Healthcare [video]", [online] Medical Daily, IBt Media Inc. © 2015, Mar. 12, 2013, retrieved from the Internet: <http://www.medicaldaily.com/google-glass-features-how-medical-uses-will-revolutionize-your-healthcarevideo-244613>, 18 pg.

"Tracking Dietary Intake Patterns of Individuals Using Social Media", Ip.Com Prior Art Database, Disclosure No. 000231487D, Oct. 2, 2013, 5 pg.

IBM Corporation, "Smart Planet: Smarter Food Supply & Aid", IP.Com Prior Art Database, Disclosure No. 000192686, Jan. 28, 2010, 7 pg.

Atzori, L. et al., "The Internet of Things: A survey," Computer Networks vol. 54, No. 15, 2010, pp. 2787-2805.

Miorandi, D. et al., "Internet of Things: Vision, Applications and Research Challenges," Ad Hoc Networks, vol. 10, No. 7, Sep. 2012, pp. 1497-1516.

Gubbi, J. et al., "Internet of Things (IoT): A Vision, Architectural Elements, and Future Directions," Future Generation Computer Systems, vol. 29, 2013, pp. 1645-1660.

Gazis, V. et al., "Wireless Sensor Networking, Automation Technologies and Machine to Machine Developments on the Path to the

(56) References Cited

OTHER PUBLICATIONS

Internet of Things," In the IEEE 16th Panhellenic Conf. on Informatics (PCI), 2012, pp. 276-282.

Bandyopadhyay, S. et al., "Lightweight Internet Protocols for Web Enablement of Sensors Using Constrained Gateway Devices," In the IEEE 2013 Int'l. Conf. on Computing, Networking and Communications (ICNC), 2013, pp. 333-340.

WIPO Appln. No. PCT/IB2016/053033, International Search Report and Written Opinion, dated Aug. 29, 2016, 9 pg.

Benzi, F, et al., "Electricity Smart Meters Interfacing the Households," IEEE Transactions on Industrial Electronics. Jan. 20, 2011;58(10):4487-94.

Alcaraz, C. et al., "Security of Industrial Sensor Network-based Substations in the Context of the Internet of Things" Ad Hoc Networks. May 1, 2013;11(3):1091-104.

IBM: List of IBM Patents or Patent Applications Treated As Related, Sep. 24, 2019, 2 pg.

Flores, C.I. et al., "Leveraging an Internet of Things to Initiate a Physical Object to Perform a Specific Act That Enhances Security", U.S. Appl. No. 16/165,205, filed Oct. 19, 2018, 52 pages.

\* cited by examiner

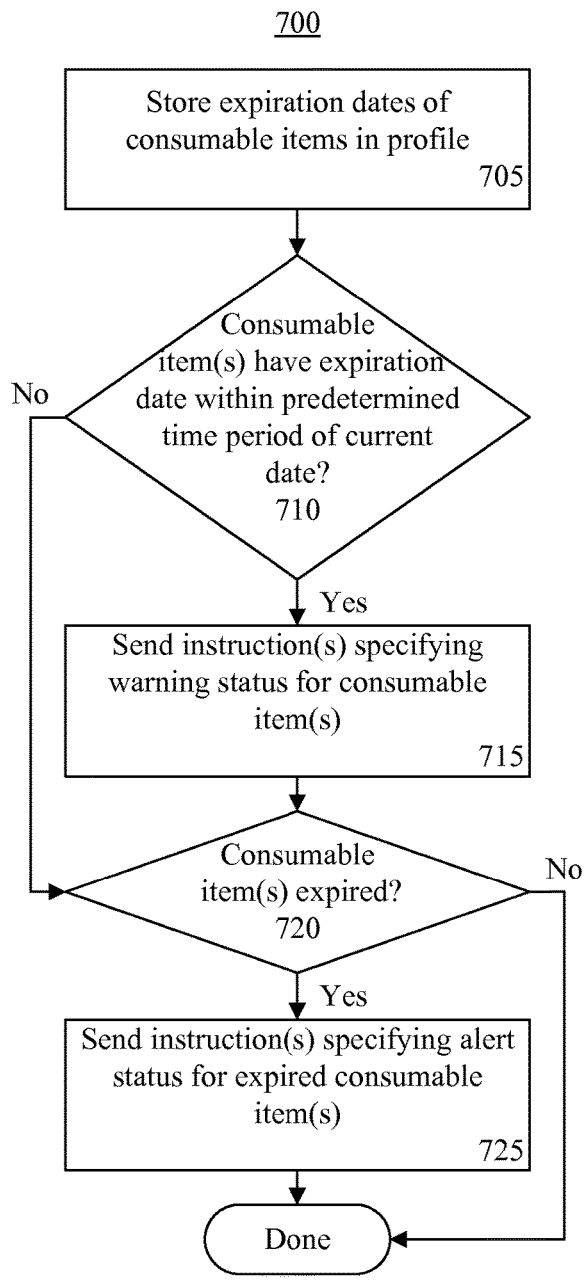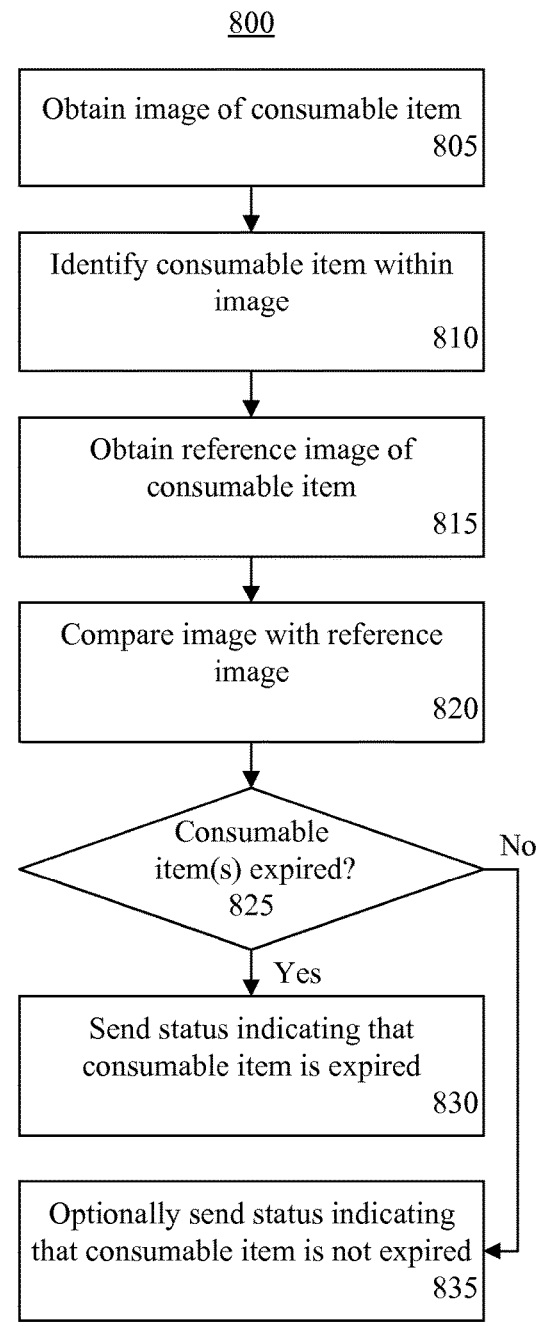
FIG. 7
FIG. 8

MONITORING AND STATUS DETECTION FOR CONSUMABLE ITEMS

BACKGROUND

The embodiments described within this disclosure relate to monitoring and status detection for consumable items. More particularly, the embodiments described herein relate to utilizing an Internet of Things for monitoring and status detection for consumable items.

Many people attempt to track their food consumption. For example, U.S. Pat. Pub. No. 2013/0273506A1 discloses "an automated food intake data acquisition and monitoring system." U.S. Pat. Pub. No. 2014/0315162A1 discloses "system and methods for monitoring food consumption." Other systems rely upon the user to manually record consumed meals, vitamins, and/or medications using a journal, whether handwritten or electronic, through social media, or the like.

Some food tracking solutions attempt to automate tracking by utilizing specialized hardware. Often, the user does not have continuous access to this specialized hardware. Without access to the specialized hardware throughout the course of one or more day(s), week(s), or month(s), it becomes unlikely that the user will obtain an accurate representation of what he or she has consumed. With respect to systems that rely upon manual data entry, the user may simply forget to log one or more meals. Inaccurate tracking is often a contributing factor to one's inability to meet particular nutritional or health objectives and may lead to more severe consequences such as illness.

Other food tracking solutions tend to focus on caloric intake without attempting to ascertain what the user is consuming and/or the context in which the consumption takes place. This may lead to situations where a user takes a medication in error or not at all, experiences adverse reactions to particular ingested items or combinations of ingested items, consumes unsafe food, or the like.

SUMMARY

A method of monitoring oral intake of consumable items may include aggregating, using a processor, oral intake information for a user from a plurality of devices belonging to a same device domain of the user in real time, comparing, using the processor, the oral intake information with a user profile of the user, and generating, using the processor, an instruction for a selected device of the plurality of devices according to the comparing. The method may include sending, using the processor, the instruction to the selected device, wherein the selected device executes the instruction.

In one aspect, the method may include determining a status of the selected device of the device domain. The instruction may also be generated according to the status of the selected device. For example, the status of the device may indicate a particular operating state and/or status such as open, closed, locked, unlocked, etc.

In another aspect, the oral intake information may specify a plurality of available consumable items. The method may include detecting removal of a consumable item from an appliance device of the device domain and marking the consumable item as unavailable responsive to the detecting.

The method may include correlating consumption data with biometric data for the user, detecting a user pattern from the correlated consumption data and biometric data, and sending an instruction, e.g., a further instruction, determined according to the biometric data for the user pattern, to the selected device of the device domain. The further instruction may specify the observed user pattern, a recommendation, or the like.

Comparing the oral intake information may include comparing a visual feature of a consumable item with a reference visual feature of an unexpired version of the consumable item (or an expired version of the consumable item) and determining whether the consumable item is expired according to the comparing of the visual feature with the reference visual feature.

Comparing the oral intake information may include comparing an expiration date of a consumable item with a current date and determining whether the consumable item is expired or is to expire within a predetermined amount of time.

Comparing the oral intake information may include retrieving ingredients for each of a plurality of variations, e.g., recipes, of a detected consumable item, comparing an allergen of the user from the user profile with the ingredients of the plurality of variations of the consumable item, and determining a probability of the consumable item including the allergen.

A system for monitoring oral intake of consumable items may include a processor programmed to initiate executable operations. The executable operations may include aggregating oral intake information for a user from a plurality of devices belonging to a same device domain of the user in real time, comparing the oral intake information with a user profile of the user, generating an instruction for a selected device of the plurality of devices according to the comparing, and sending the instruction to the selected device, wherein the selected device executes the instruction.

The processor may be programmed to initiate executable operations including determining a status of the selected device of the device domain. The instruction may also be generated according to the status of the selected device. For example, the status of the device may indicate a particular operating state such as open, closed, locked, unlocked, etc.

In one aspect, the oral intake information may specify a plurality of available consumable items. The processor may be programmed to initiate executable operations including detecting removal of a consumable item from an appliance device of the device domain and marking the consumable item as unavailable responsive to the detecting.

The processor may be programmed to initiate executable operations including correlating consumption data with biometric data for the user, detecting a user pattern from the correlated consumption data and biometric data, and sending a further instruction, determined according to the biometric data for the user pattern, to the selected device of the device domain. The further instruction may specify the observed user pattern, a recommendation, or the like.

Comparing the oral intake information may include comparing a visual feature of a consumable item with a reference visual feature of an unexpired version of the consumable item (or an expired version of the consumable item) and determining whether the consumable item is expired according to the comparing of the visual feature with the reference visual feature.

Comparing the oral intake information may include comparing an expiration date of a consumable item with a current date and determining whether the consumable item is expired or is to expire within a predetermined amount of time.

Comparing the oral intake information may include retrieving ingredients for each of a plurality of variations, e.g., recipes, of a detected consumable item, comparing an allergen of the user from the user profile with the ingredients of the plurality of variations of the consumable item, and determining a probability of the consumable item including the allergen.

A computer program product may include a computer readable storage medium having program code stored thereon for monitoring oral intake of consumable items. The program code may be executable by a processor to perform a method. The method may include aggregating, using a processor, oral intake information for a user from a plurality of devices belonging to a same device domain of the user in real time, comparing, using the processor, the oral intake information with a user profile of the user, and generating, using the processor, an instruction for a selected device of the plurality of devices according to the comparing. The method may include sending, using the processor, the instruction to the selected device, wherein the selected device executes the instruction.

In one aspect, the method may include determining a status of the selected device of the device domain. The instruction may also be generated according to the status of the selected device. For example, the status of the device may indicate a particular operating state such as open, closed, locked, unlocked, etc.

In another aspect, the oral intake information may specify a plurality of available consumable items. The method may include detecting removal of a consumable item from an appliance device of the device domain and marking the consumable item as unavailable responsive to the detecting.

The method may also include correlating consumption data with biometric data for the user, detecting a user pattern from the correlated consumption data and biometric data, and sending an instruction, e.g., a further instruction, determined according to the biometric data for the user pattern, to the selected device of the device domain. The further instruction may specify the observed user pattern, a recommendation, or the like.

Comparing the oral intake information may include comparing a visual feature of a consumable item with a reference visual feature of an unexpired version of the consumable item (or an expired version of the consumable item) and determining whether the consumable item is expired according to the comparing of the visual feature with the reference visual feature.

Comparing the oral intake information may include comparing an expiration date of a consumable item with a current date and determining whether the consumable item is expired or is to expire within a predetermined amount of time.

Comparing the oral intake information may include retrieving ingredients for each of a plurality of variations, e.g., recipes, of a detected consumable item, comparing an allergen of the user from the user profile with the ingredients of the plurality of variations of the consumable item, and determining a probability of the consumable item including the allergen.

BRIEF DESCRIPTION OF THE DRAWINGS

FIG. 7 is a flow chart illustrating an exemplary method of expiration status detection.

FIG. 8 is a flow chart illustrating another exemplary method of expiration status detection.

DETAILED DESCRIPTION

Figure 1:
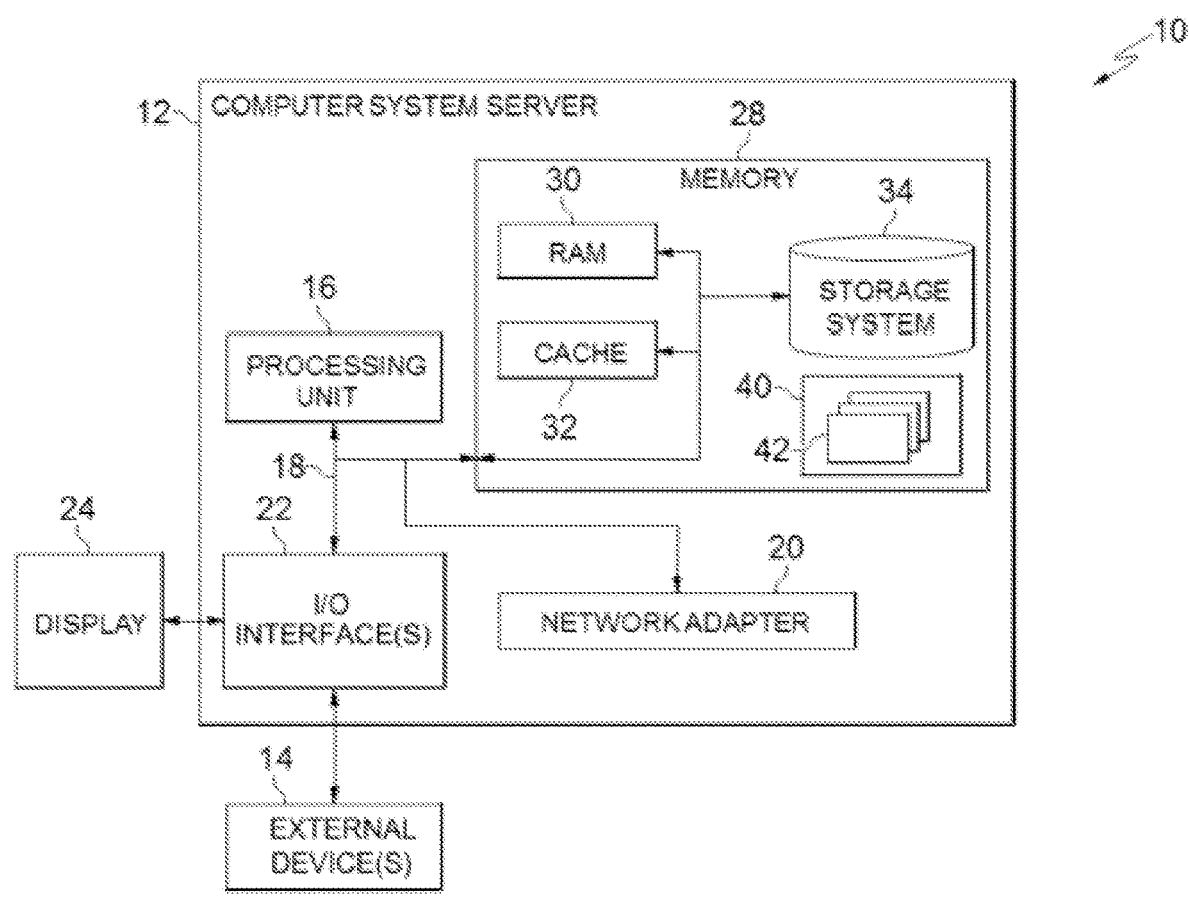
FIG. 1 depicts a cloud computing node according to an embodiment of the present invention.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to monitoring and status detection for consumable items. More particularly, this disclosure relates to utilizing an Internet of Things for performing monitoring and status detection for consumable items. In accordance with the inventive arrangements described herein, user consumption of consumable items such as food, medications, and/or vitamins, may be tracked using an Internet of Things (IOT). As defined within this disclosure, the term "Internet of Things" or "IOT" means a computing environment in which devices are embedded in physical objects which enable the physical objects to achieve greater value and service by exchanging data with other systems and/or other connected devices. Each physical object is uniquely identifiable through its embedded device(s) and is able to interoperate within an Internet infrastructure.

One or more devices belonging to a same device domain, for example, may be used to collect and/or generate oral intake information for a user. A device domain, in general, refers to a logical grouping of devices part of an IOT environment. The devices may be logically grouped according to individual, location, group association, etc. The oral intake information may be aggregated from one or more of the devices of the device domain. In tracking, the particular item(s) being consumed may be identified as part of oral intake information that is stored within the system. Further, the quantity of items consumed, e.g., portions, may also be determined as part of the oral intake information.

In one aspect, a historical record may be created from the oral intake information for the user. The system, for example, may determine user patterns relating to health and behavior. Further, the system may determine user patterns relating to health and behavior for a larger set of devices and/or users, e.g., across multiple device domains. The larger, or "global," health and behavior patterns may be applied to a particular user to determine recommendations, provide guidance, perform comparisons, or the like.

In another aspect, the user may be associated with a user profile stored in a computer readable storage medium. The user profile may include, but is not limited to, the oral intake information (e.g., including historical oral intake information), one or more objectives, medical information, which may include allergy information, and/or personal biological response information for the user. Utilizing the user profile, a system may detect consumable items, e.g., in real time using one or more devices of a device domain of an IOT, and determine a status of the one or more consumable items. The status may be sent to a device of the device domain of the user. The status may be sent in real time. The status may be determined, at least in part, according to a comparison of the consumable item(s) and/or attributes thereof, with the user profile.

The term "consumable item," as defined herein, refers to an object that may be orally ingested by a user. In one aspect, a consumable item includes items consumed for purposes of medical treatment, nourishment, health, and/or wellness. The consumption of a consumable item by a user, under normal circumstances, e.g., when following known instructions and/or standard protocols for perishable items, may not be harmful to the user. Examples of consumable items may include, but are not limited to, food, medication, vitamins, health supplements, and the like. It should be appreciated, however, that the inventive arrangements described herein may also be used to prevent consumption of items that, while consumable, are not digestible. For example, the system may recognize particular items that may be, or are about to be, consumed by a child such as small toys or the like that are not digestible and provide an alert status.

A "status," as applied to a consumable item, is an indication of whether a particular consumable item, or consumable items, may be orally ingested by a user. Exemplary statuses of consumable items may include, but are not limited to, "about to expire," "expired," "allergen," "do not consume," "consume," "non-digestible," etc. A status may be sent as an electronic message and, as such, may include additional content beyond the general indication of whether the particular consumable item(s) may be orally ingested.

For example, a status may be sent as part of an instruction or instruction(s). The instruction(s) are executable and, when received and executed by a device of a device domain of a user, cause the device to initiate one or more executable operations. Such executable operations may include providing notifications on a display screen, providing audible notifications, sending electronic messages, locking or unlocking a smart appliance type of device or other device, or the like. As will be described in further detail herein, the status of one or more consumable items may be determined through an analysis of the user profile and interaction of data stored therein such as oral intake information, oral intake instructions, user objectives, and the like.

Several additional definitions that apply throughout this document now will be presented. As defined herein, the term "device domain" means a plurality of devices of an IOT that are associated with a particular user or group of associated users. Devices within a same device domain share information directly with one another or with one another via a remote or other communication system or network. An exemplary device domain may include a personal computer of a user, a mobile phone of the user, a smart watch of the user, smart glasses of the user, smart appliances of the user, etc. A device domain may be extended to include devices belonging to a group of related users, e.g., devices of family members or devices belonging to members of a business organization.

As defined herein, the term "device community" means a set of one or more device domains and at least one community IOT concentrator to which devices in the one or more device domains are communicatively linked.

As defined herein, the term "global IOT community" means a system, including at least one enterprise IOT concentrator, which acquires and processes information from a plurality of device communities.

As defined herein, the term "community IOT concentrator" means a system, including at least one processor and memory, configured to provide analytical processing and data in support of a set of one or more device domains.

As defined herein, the term "enterprise IOT concentrator" means a system, including at least one processor and memory, configured to provide analytical processing and data in support of a set of one or more device communities.

As defined herein, the term "user pattern" means data representing traits, acts, tendencies and/or observable characteristics of a user relating to oral intake of the user. A user pattern may be generated for a user by processing data generated by a user's interaction with one or more devices of a device domain.

For purposes of simplicity and clarity of illustration, elements shown in the figures have not necessarily been drawn to scale. For example, the dimensions of some of the elements may be exaggerated relative to other elements for clarity. Further, where considered appropriate, reference numbers are repeated among the figures to indicate corresponding, analogous, or like features.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16. Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
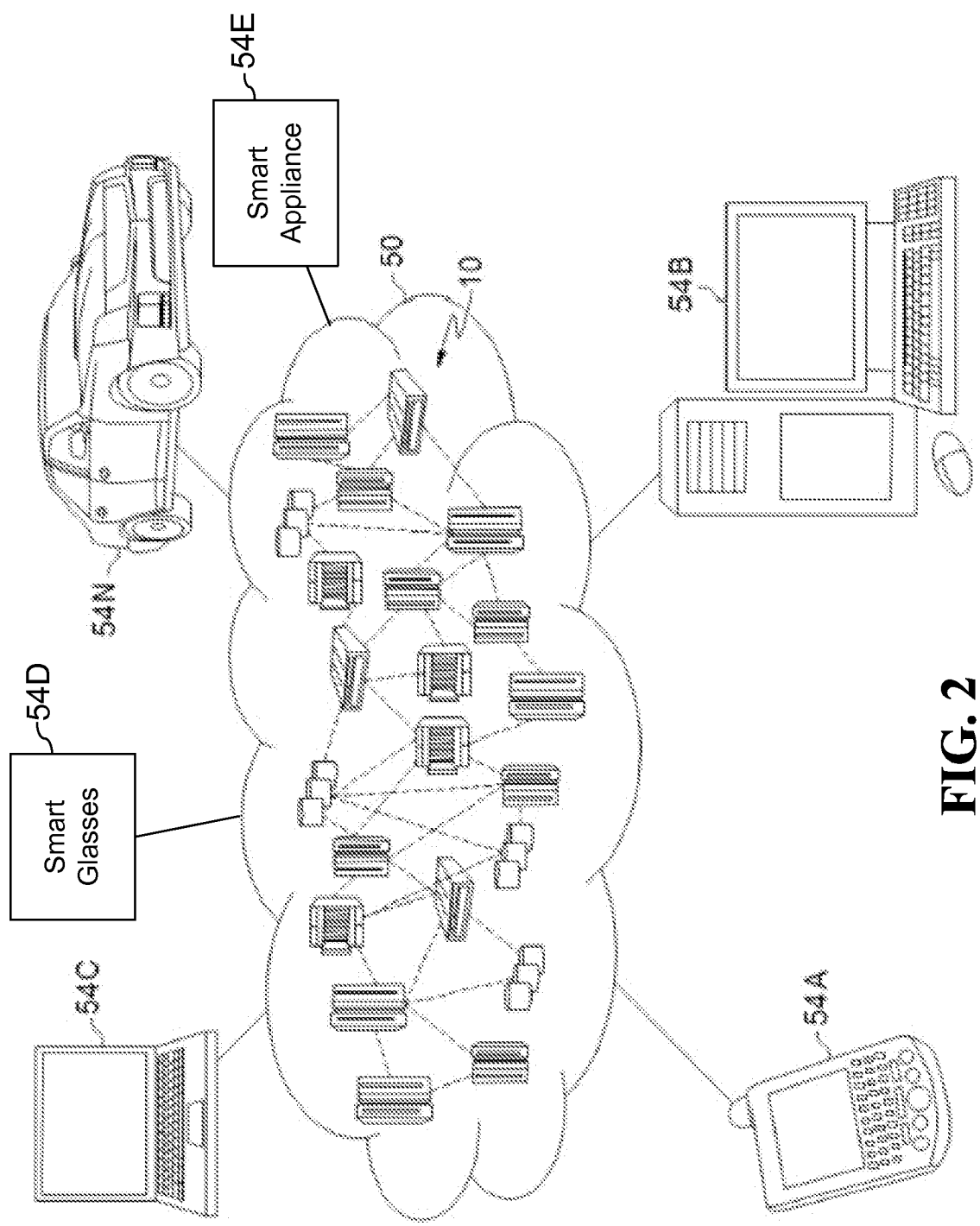
FIG. 2 depicts a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, smart glasses 54D, smart appliance 54E, and/or automobile computer system 54N may communicate. Examples of smart appliance 54E may include, but are not limited to, microwaves, refrigerators, medication dispensers, pantries, and the like. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
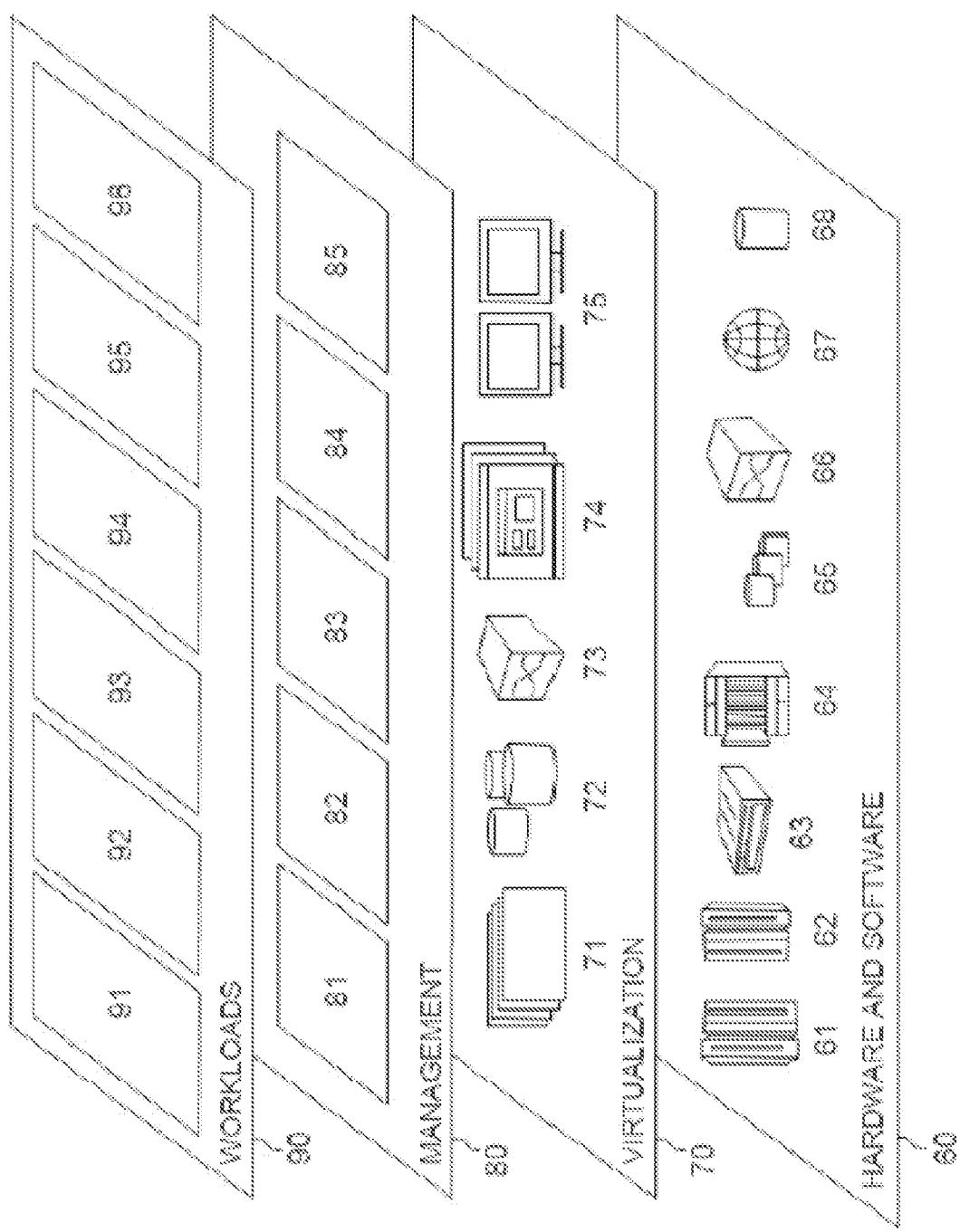
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and oral intake monitoring and status detection of consumable items 96.

Figure 4:
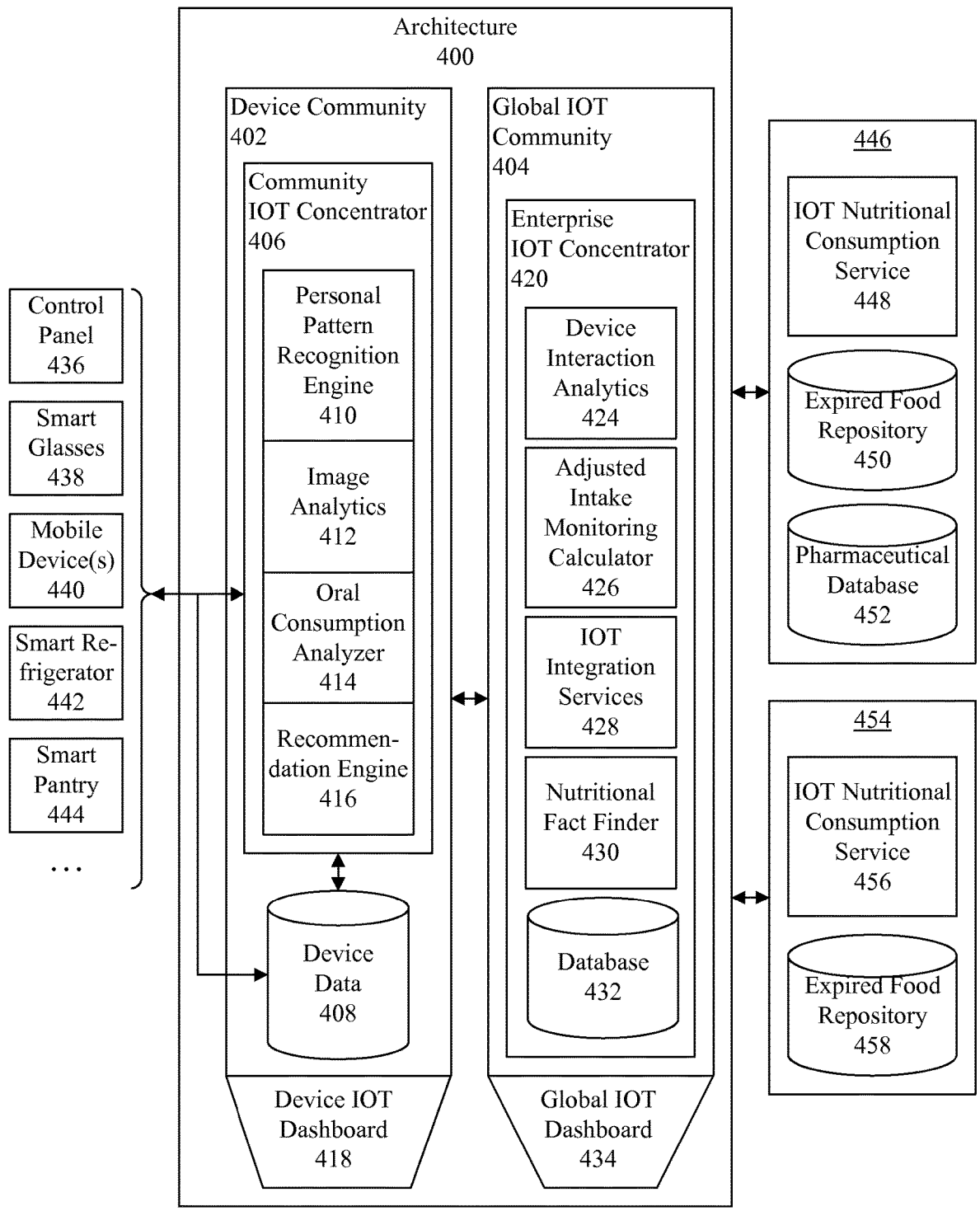
FIG. 4 is a block diagram illustrating an exemplary architecture for oral intake monitoring and status detection of consumable items.

FIG. 4 is a block diagram illustrating an exemplary architecture 400. In one arrangement, architecture 400 may be used to implement oral intake monitoring and status detection of consumable items 96 of FIG. 3. It should be appreciated that architecture 400 is provided for purposes of illustration and, as such, is not intended to limit the various embodiments described herein.

As pictured, architecture 400 may include a device community 402, a global IOT community 404, a device IOT dashboard 418, and a global IOT dashboard 434. Device community 402 may include a community IOT concentrator 406 and device data 408. Community IOT concentrator 406 may include personal pattern recognition engine 410, image analytics 412, oral consumption analyzer 414, and recommendation engine 416. Global IOT community 404 may include an enterprise IOT concentrator 420. Enterprise IOT concentrator 420 may include device interaction analytics 424, an adjusted intake monitoring calculator 426, IOT integration services 428, a nutritional fact finder 430, and a database 432.

As pictured, one or more devices belonging to an IOT may be communicatively linked with architecture 400. A control panel 436, smart glasses 438, one or more mobile devices 440, a smart refrigerator 442, a smart pantry 444, and any other devices including smart appliances, biological sensors, medical and/or health monitors, etc., may be communicatively linked with architecture 400 and, more particularly, to community IOT concentrator 406. For purposes of illustration, devices 436-444 may be part of a same device domain. For example, each of devices 436-444 may be associated with, or used by, a same user. In another example, each of devices 436-444 may be associated with, or used by, a same group of two or more related users, e.g., family members, members of business or other organization, or the like.

Architecture 400, as implemented and executed within one or more data processing systems, may also be coupled to one or more other systems. For example, as pictured, architecture 400 may be coupled to one or more external computing systems (systems) 446 and 454. Systems 446 and 454 may be owned by, or otherwise associated with, a third party such as a store, retailer, or other provider of goods and/or services. System 446 may include an IOT nutritional consumption service 448, an expired food repository 450, and a pharmaceutical database 452. System 454 may include an IOT nutritional consumption service 456 and an expired food repository 458. In one exemplary implementation, systems 446 and 454 may be implemented as cloud based systems that are utilized by the third parties described. In another aspect, systems 446 and 454 may be incorporated as part of architecture 400.

Control panel 436 may be implemented as a Web-based interface, e.g., a browser, an application, or the like, that executes on a device of a user. Control panel 436 provides an interface through which a user may enter data, retrieve data, view real time data, and otherwise access data stored in the user's profile, e.g., within database 408 and/or 432. For example, a user working through control panel 436 may enter any information to be included in the user's profile including, but not limited to, personal data, medical history, prescribed medications, dietary and/or nutritional objectives, allergies to particular consumable items or other environmental factors, and the like. Control panel 436 may also operate as an interface through which statuses for consumable items may be provided to the user.

Smart glasses 438, mobile devices 440, and/or a data processing system providing control panel 436 may include one or more applications executing therein. Further, devices 438, 440, and/or 436 (i.e., the data processing system providing control panel 436) may include one or more sensors including, but not limited to, an input audio transducer (e.g., a microphone) to capture audio, an output audio transducer (e.g., a speaker) to play audio, a camera to capture images and/or video, an accelerometer to capture acceleration data, a global positioning system (GPS) receiver to determine location, an eye tracking system to capture eye movements of a user, a gyroscope to capture orientation information, or the like. In another example, smart glasses 438, mobile devices 440, and/or control panel 436 may include one or more biological sensors that may be configured to capture heart rate, blood pressure, or the like.

Smart refrigerator 442 may include a display screen located on an outer portion of smart refrigerator 442 to display messages, a microphone to receive audio data, a keyboard entry device (which may also be implemented as a touchscreen), or the like. Smart refrigerator 442 may include one or more cameras located internally that permit smart refrigerator 442 to capture image data of consumable items stored therein. Smart pantry 444 may be similarly configured with one or more I/O devices allowing a user to interact with smart pantry 444 and with one or more cameras located inside that permit smart pantry 444 to capture images of the objects located inside. Both smart refrigerator 442 and smart pantry may include I/O devices that allow the devices to communicate with community IOT concentrator 406.

Data received from devices 436-444, e.g., oral intake information, may be stored in device data 408. Data stored in device data 408 may include any of the audio, images, video, acceleration data, gyroscopic data, biological sensor data, and the like generated by devices 436-444. In one aspect, device data 408 may store raw, e.g., unprocessed, data received from one or more of devices 436-444. Device data 408 may represent data from the plurality of devices 436-444 and may be aggregated. Device data 408 may be stored within a computer readable storage medium. Device data 408 may be stored within a data structure such as one or more tables, files, eXtensible Markup Language (XML) formatted data, a database, or the like. The various modules of community IOT concentrator 406 may also read and/or store data within device data 408.

In one arrangement, device data 408 and database 432 may operate cooperatively with one another. For example, data that may be created, revised, updated, and/or deleted may be periodically shared and/or synchronized with database 432. Further, one or more subsets of data that may be created, revised, updated, and/or deleted within database 432 may be periodically shared and/or synchronized with device data 408.

Personal pattern recognition engine 410 may analyze device data 408 to detect user patterns within the collected and aggregated device data 408. The user patterns may be oral intake consumption patterns, patterns of biological response data or events coupled with particular oral intake of one or more consumable items, or the like. Image analytics 412 may perform image processing, identify particular features of images, compare two or more images and/or visual features, and the like. Oral consumption analyzer 414 may be configured to determine the identity of particular food items from captured images. Oral consumption analyzer 414 may also determine an amount, or quantity, of one or more consumable items consumed by a user. Recommendation engine 416 may be configured to evaluate the user profile and overall consumption, e.g., oral intake information, for a user or users and send status information for user(s) to one or more of devices 436-444. In one aspect, recommendation engine 416 may determine and send a status responsive to a particular event, from time-to-time, or the like.

Referring to global IOT community 404, enterprise IOT concentrator 420 may interact with community IOT concentrator 406 and with systems 446 and/or 454. In general, whereas device community 402 operates at the device domain level, one or more modules of global IOT community 404 and enterprise IOT concentrator 420 may operate across multiple device domains. One or more modules, however, may provide services to community IOT concentrator 406 on a per user basis (e.g., a device domain specific basis).

Device interaction analytics 424 may aggregate, evaluate, and/or compare device data from two or more different device domains. Further, device interaction analytics 424 may track interactions among devices of different device domains and/or within a particular device domain. For example, device interaction analytics 424 may determine which devices are communicating with one another, when such devices are communicating with one another, the location of such devices, and the like. Device interaction analytics 424 may also be configured to determine when a user, or users, are accessing devices across different domains. For example, device interaction analytics 424 may determine that a user is using a device such as a mobile device belonging to a first device domain. Device interaction analytics 424 may further determine that the same user is using, or has used, a different device such as a kiosk that belongs to a different device domain, e.g., a device domain of a physician's office.

Adjusted intake monitoring calculator 426 may receive information from database 432. Database 432 may store information from systems 446 and/or 454 that was obtained through IOT integration services 428. In one aspect, adjusted intake monitoring calculator 426 may adjust statuses according to data received from one or more other systems. For example, consider a case where system 446 supports a pharmacy. System 446 may upload data to enterprise IOT concentrator 420 indicating that a user has just refilled a prescription. The refill information for the prescription may be shared with enterprise IOT concentrator 420 and stored in database 432. Community IOT concentrator 406 may request periodic updates from enterprise IOT concentrator 420 and database 432 and store the obtained data in device data 408 for efficient data retrieval. Subsequently, personal pattern recognition engine 410, recommendation engine 416, image analytics 412, and/or oral consumption analyzer 414 may determine that the user has consumed a last pill from the same prescription that was refilled. As such, community IOT concentrator 406 may determine that no alert for a refill need be sent to a device of the user since the refill has already been initiated and/or processed.

IOT integration services 428 may externalize application services to business partners via the Internet. For example, IOT integration services 428 may communicate with system 446 and/or system 454. IOT integration services 428 may communicate with IOT nutritional consumption service 448 of system 446 and with IOT nutritional consumption service 456 of system 454. Any data uploaded or otherwise obtained from systems 446 and/or 454 may be received by IOT integration services 428 and stored in database 432.

Nutritional fact finder 430 may analyze nutritional data stored in database 432 to obtain data relating to user purchases of consumable items such as food, vitamins, medications, and the like. For example, participating merchants may create a customer profile that stores a historical record of purchased consumable items that may be uploaded from the point of sale to system 446 and/or system 454. As noted, one or more components within systems 446 and/or 454 such as pharmaceutical database 452 and/or expired food repository 458 may be co-managed by third parties such as the point of sale owner (or merchant) and/or third parties other than the point of sale owner such as pharmaceutical firms, food manufacturers, or the like. Any attributes of the consumable items, e.g., oral intake instructions, nutritional data, ingredients, expiration data, etc., relating to purchased consumable items may also be uploaded to system 446 and/or system 454. IOT integration services 428 may store the historical record of purchased consumable items for the user within database 432 as part of a user profile. Nutritional fact finder 430 may access IOT integration services 428 to obtain attributes of the consumable items, as may be needed, from systems 446 and/or 454. In one aspect, nutritional fact finder 430 may be configured on a per user basis to obtain additional attributes of consumable items relating to health and/or wellness from one or more other online accessible databases or Websites that the user indicates are acceptable sources of information.

Database 432 may be a health and wellness database. Database 432 may be stored in a computer readable storage medium. In addition to storing information as previously described within this disclosure, database 432 may also store user profiles. A user may access his or her user profile through control panel 436. Further, community IOT concentrator 406 and/or enterprise IOT concentrator 420 may read from or write to the user profiles within database 432.

Systems 446 and/or 454 represent computing infrastructure of one or more business entities that choose to opt-in to utilizing architecture 400. For example, system 446 may be for a pharmacy and include an expired food repository 450 specifying expiration data for various consumable items whether food, medicines, vitamins, or the like. Pharmaceutical database 452 may store medicines (e.g., pharmaceuticals) along with other attributes such as oral intake instructions, side effects, potential adverse reactions that may occur when taking the medication, known interactions with other medications, and the like. System 454 may be for a grocery store and include expired food repository 458.

Device IOT dashboard 418 may be implemented as a Web-interface through which one or more authorized users designated as a device domain owner may access the aforementioned information across each of the various devices of a same domain. As an illustrative example, if the device domain is for a family, the device domain owner may be a parent that is checking data, e.g., device data and/or user profiles, across one or more or all devices in the same device domain, e.g., the devices belonging to different members of the device domain owner's family. In another illustrative example, the device domain may be for a medical practice while the device domain owner is an authorized user such as the doctor or other member of the medical practice. The device domain owner may be able to access data across the various devices that are part of the device domain. The devices may be devices belonging to staff or employees of the medical practice and/or of patients that have chosen to opt-in to the service.

Global IOT dashboard 434 may be implemented as a Web-interface through which one or more users designated as global device domain owners may access data across a plurality of different device domains. For example, a plurality of medical practices may use information and services from architecture 400 with a global device domain owner accessing data for one or more or all of the member medical practices. The various member medical practices may be subsidiaries of a larger entity, or the like.

Food Intake Monitoring

Figure 5:
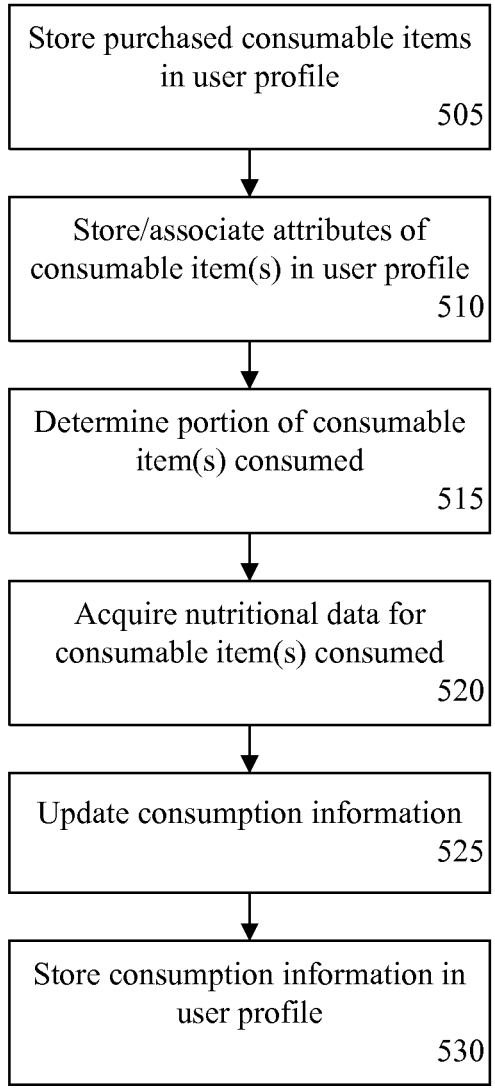
FIG. 5 is a flow chart illustrating an exemplary method of oral intake monitoring.

FIG. 5 is a flow chart illustrating an exemplary method 500 of food intake monitoring. Method 500 may be performed by a data processing system (system) utilizing the architecture described with reference to FIG. 4. FIG. 5 illustrates an example where architecture 400 may be used to collect food label information for consumable items that the user plans on consuming orally. Further, estimates of portions consumed by a user may be estimated.

In block 505, the system may store purchased consumable items in a user profile of the user within database 432. In one aspect, purchased consumable items may be obtained by IOT integration services 428 by requesting information from point of sale locations that opt-in to using the system. For example, one or more grocery stores may opt-into being leveraged by architecture 400 and utilize a system such as system 446 and/or 454. The stores may create customer (e.g., user) profiles of consumable items purchased by the user. The customer profiles, which may specify a history of purchased consumable items, may be uploaded through system 446 and/or IOT integration services 428 of architecture 400 and stored in database 432. As noted, device data 408 and database 432 may operate cooperatively to share data and/or subsets of data as previously described. Thus, a user may access the information stored in database 432 and/or device data 408 through control panel 436.

In one exemplary implementation, responsive to a user checking out with one or more consumable items, the point of sale system may document the consumable items purchased in the consumer profile within a consumer profile database. IOT integration services 428 may be triggered by nutritional fact finder 430 to query or poll IOT nutritional consumption service 448 or 456 for the point of sale and obtain the purchased consumable items. In one aspect, the purchased consumable items may only be obtained from sources that the user has granted access or otherwise identified as a trusted source of such information. Any purchased consumable items may be considered an available consumable item for purposes of determining status as described within this disclosure.

In another arrangement, consumable items being purchased may be captured by one or more devices of the user's device domain. For example, a camera of smart glasses 438 and/or of mobile device 440 may be used to capture an image of a consumable item being purchased. The image may be captured as the user selects the item from a shelf, as the user places the item in his or her shopping cart, etc. The image of the consumable item may be provided to image analytics 412 to identify the particular consumable item. The consumable item may be stored in database 408. Any data stored in device data 408 may be shared and/or synchronized with database 432 as previously described.

In block 510, the system may associate attributes such as oral intake rules and/or nutritional data with the purchased consumable items in the user profile stored in database 432 or device data 408. In one aspect, oral intake rules and/or nutritional data for purchased consumable items may be obtained from the point of sale locations. For example, such information may be stored and retrieved by nutritional fact finder 430 triggering IOT integration services 428 to obtain information from IOT nutritional consumption service 448 and/or 456. The attributes may be stored within database 432 in association with the corresponding consumable items within the user profile. Attributes stored in database 432 may also be propagated to device data 408.

In another aspect, one or more of the user's devices, e.g., smart glasses 438 and/or mobile device 440, may be used to obtain an image of label information for consumable items being purchased. Image analytics 412 may, for example, obtain a product code or other identifier that may be used to store appropriate information in device data 408. Any product code or other information stored in device data 408 may be propagated to database 432 as previously described. In another example, image analytics 412 may use optical character recognition to determine oral intake instructions and/or nutritional data directly from a label of the consumable item. Image analytics 412, for instance, may determine the instructions for medication using optical character recognition on an image of a label of a medication. In any case, the resulting oral intake instructions and/or nutritional data may be stored in device data 408 in association with the corresponding purchased consumable items and/or may be propagated to database 432.

In one aspect, the attributes that are determined in block 510 may include expiration information. Expiration information, e.g., an expiration date, for a consumable item may be obtained from the point of sale location as part of the uploaded attributes for the consumable item(s) purchased. In another aspect, expiration data may be obtained directly from a label of the consumable item using optical character recognition to determine the expiration date.

In performing blocks 505-510, it should be appreciated that the system may maintain a record of what is on-hand for the user. The record of purchased consumable items may be used for purposes of recommending particular consumable items at different times since the system considers such items to be available to the user. As used herein, an "available consumable item" is a consumable item that is purchased by the user or a consumable item identified within a device of a device domain of the user such as a smart refrigerator, a smart pantry, or the like. An available consumable item is further a consumable item that has not been identified by the system as being consumed or expired.

In block 515, the system may determine the portion of one or more consumable items, e.g., food, consumed by the user. One or more IOT devices of the user may be used to monitor the servings that the user consumes. For example, a user may grab a portion of chips or make a plate of food. Smart glasses 438 may be used to estimate how much food was actually consumed by comparing an initial image of the food prior to the start of consumption by the user and an image of the food after consumption by the user.

For example, oral consumption analyzer 414 may recognize the particular food items from the image and quantify the food in the image. This process may be performed on the initial image and on a subsequent image of the food to estimate the amount of food represented in each image. Oral consumption analyzer 414 may calculate a difference between the two estimates where the difference is the amount of food consumed by the user. This result may be stored in device data 408 and propagated to database 432 as part of the user profile.

In block 520, the system may acquire the nutritional data for the consumable item(s) that were consumed. For example, oral consumption analyzer 414 may query nutritional fact finder 430 for the nutritional data. Nutritional fact finder 430 may retrieve the nutritional data from database 432. The nutritional data may include caloric amounts for the foods. In block 525, adjusted intake monitoring calculator 426 may update the consumption data in accordance with actual nutritional data for the consumed portion of the food. For example, adjusted intake monitoring calculator 426 may calculate the number of calories consumed by the user according to the difference estimate from the images, the particular food identified as being eaten, and the nutritional data for the food.

In block 530, adjusted intake monitoring calculator may store the resulting consumption data in the profile for the user within database 432 and subsequently within device data 408. The consumption data may be stored as part of a historical record within the user profile of what the user has eaten. As used herein, the term "consumption data" refers to consumable items, or portions thereof, determined to have been orally ingested by a user. The consumption data may be historical data in that the consumption data may be recorded over defined periods of time. In one arrangement, oral intake information may include consumption data.

FIG. 5 illustrates an example where the system may record more accurate data for consumption by the user. More often than not, users do not consume an entire serving. The arrangements disclosed allow a more accurate recording of what is actually consumed by the user. In another aspect, the system may mark those purchased consumable items that have been determined to be consumed as unavailable or remove the consumable items from the user's profile.

Real Time Dietary Recommendation

Figure 6:
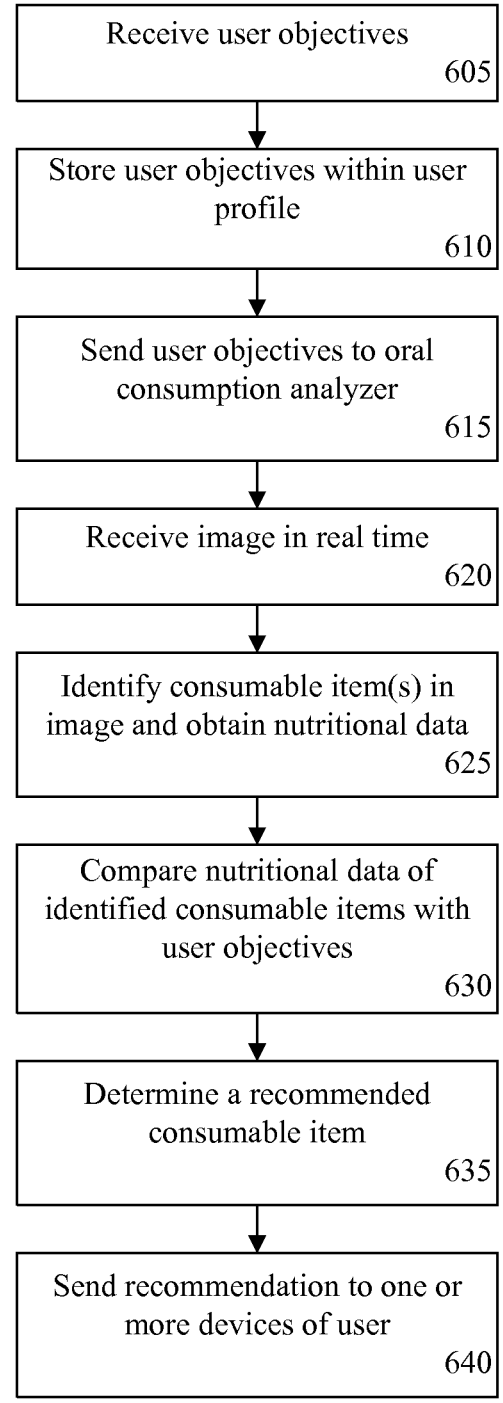
FIG. 6 is a flow chart illustrating an exemplary method of providing real time dietary recommendations.

FIG. 6 is a flow chart illustrating an exemplary method 600 of providing real time dietary recommendations. Method 600 may be performed by a data processing system (system) utilizing the architecture described with reference to FIG. 4.

In block 605, the system may receive one or more user objectives. The objectives may be dietary objectives, nutritional objectives, or the like. In one example, the objectives may be received from a user through control panel 436. In block 610, the system may store the user objectives within the user profile within device data 408 and subsequently within database 432. In block 615, the system may send the user objectives to oral consumption analyzer 414. In block 620, the system may receive an image in real time. The image may be of one or more consumable items as captured by smart glasses 438 or mobile device 440.

In block 625, the system may identify the consumable items from within the image as oral intake information. For example, oral consumption analyzer 414 may identify a plurality of different consumable items within the image. Further, the system may obtain nutritional data for the identified consumable items. In one aspect, oral consumption analyzer 414 may query database 408 for nutritional data for the identified consumable items. For example, nutritional data may be propagated from database 432 to device data 408.

In block 630, the system may compare the nutritional data for the identified consumable items with the user objectives. For example, the system may determine which of the consumable items identified in the image is compliant with one or more of the user objectives. In block 635, the system may determine a recommended consumable item. For example, recommendation engine 416 may select an identified consumable item that complies with the user objectives. In block 640, the system may send the recommendation to the user. As noted, the recommendation may be an instruction or instructions specifying a status such as "recommended" or "not recommended". For example, each consumable item in the image may be in the field of view of the user wearing smart glasses 438. The identified consumable items may be highlighted or visually distinguished with annotations or colors indicating "recommended" or "not recommended".

FIG. 6 illustrates an exemplary implementation where the system may provide real time dietary information to users. The real time information may be provided through control panel 436 or another one of the devices of the user's device domain. In one example, a user may be shopping at a grocery store and wish to purchase a consumable item such as peanut butter. Smart glasses 438 may detect three different brands of peanut butter on the shelf. In one aspect, architecture 400 may determine the most appropriate brand of peanut butter for the user.

For example, oral consumption analyzer 412 may identify the three different brands of peanut butter from an image. Oral consumption analyzer 414 may obtain nutritional data including ingredients for each brand of peanut butter and compare the nutritional data with the objectives of the user and/or with progress of the user in meeting one or more nutritional objectives based on consumption data stored in device data 408. Recommendation engine 416 may send the instructions to the user specifying a status for one or more of the consumable items (e.g., the different brands of peanut butter). In one aspect, smart glasses 438 may highlight the suggested brand of peanut butter with green and highlight the other brands of peanut butter in red or otherwise indicate that one brand is preferred over the others in order to reach a defined user objective such as reduce calories, eat organically, etc. In this example, the status of each consumable item may be "recommended" or "not recommended".

In another example, location of the user may be utilized by recommendation engine 416 to determine nearby shopping locations. For instance, recommendation engine 416 may recommend shopping at a nearby health store, e.g., within a predetermined distance of the user, as opposed to selecting a more generalized grocery store that may also be within the predetermined distance.

In still another example, smart refrigerator 442 and/or smart pantry 444 may be utilized to deliver recommendations from recommendation engine 416. For instance, architecture 400 may receive a message that smart refrigerator 442 and/or smart pantry 444 is opened (e.g., has a status of open). Responsive to opening smart refrigerator 442 and/or smart pantry 444, recommendation engine 416 may determine a suggested consumable item, e.g., a snack, for the user that is consistent with the user's objectives. The suggested consumable item may be one that is considered available as previously discussed and that complies with the user's objectives. For example, the suggested consumable item may be one that has been purchased or one that smart refrigerator 442 and/or smart pantry 444 has determined to be located inside using, for example, image processing. Alternatively the suggested consumable item may be one that is identified from an image captured by smart glasses 438 while the user looks through smart refrigerator 442. Smart refrigerator 442 and/or smart pantry 444, for example, may send a list of consumable items stored therein to architecture 400 for storage in database 408. Recommendation engine 416 may consult the list of available consumable items in order to make a selection that complies with the stored user objectives. This example also illustrates interoperability of devices in the device domain. In the above example, a status of a device such as a smart refrigerator or smart pantry being opened may be used to initiate operations in another device such as the smart glasses in providing instructions that may cause the smart glasses to display a recommendation and/or highlight a particular consumable item in the smart appliance.

In further illustration, recommendation engine 416 may send instructions specifying a status such as "try an apple," which may be provided to the user's smart glasses 438, to smart refrigerator 442, and/or smart pantry 444, e.g., the device that was initially opened. The apple may be a consumable item that is listed in the contents of smart refrigerator 442 and/or smart pantry 444. In receiving the message from architecture 400 specifying a particular consumable item, smart refrigerator 442 and/or smart pantry 444 may determine the location of the consumable item therein. Accordingly, in addition to displaying the consumable item suggestion, smart refrigerator 442 and/or smart pantry 444 may also provide the location of the suggested food item, e.g., "on the third shelf" or "in the crisper." Thus, the user is provided with a suggestion in real time responsive to opening the smart appliance.

In another example, the system may monitor consumption data for a user and compare the historical consumption data with the one or more objectives from the user profile. Based upon whether the user is meeting the objectives, the system may send lock or unlock instructions to one or more smart appliances such as the smart refrigerator and/or the smart pantry to either allow or disallow removal of food.

In still another example, a user may be shopping. The user may initiate a query from mobile device 440 or smart glasses 438 to smart refrigerator 442 and/or smart pantry 444 inquiring whether the appliance includes a particular grocery item. The smart appliance may respond to the querying device by indicating whether the smart appliance does include or contain the particular item specified by the query and/or an amount of the item.

Expiration Detection Examples

FIG. 7 is a flow chart illustrating an exemplary method 700 of expiration status detection. Method 700 may be performed by a data processing system (system) utilizing the architecture described with reference to FIG. 4.

In block 705, expiration dates for consumable items may be stored in the user profile. In one arrangement, expiration dates for consumable items may be determined and stored in database 432. In one aspect, one or more devices of a device domain of the user may capture an image of a food expiration date that may be determined using image analytics 412 and stored in device data 408. As noted, data may be shared and/or synchronized between database 432 and device data 408. In another example, a point of sale, e.g., a grocery store, may provide expiration dates for purchased consumable items as part of the consumer profile that may be uploaded to architecture 400.

In block 710, the system may determine whether one or more consumable items have expiration dates within a predetermined time period of the current date. As the expiration date of one or more consumable items approaches, recommendation engine 416 may send instructions specifying statuses to one or more of devices 436-444 of the approaching expiration of the consumable items. For example, recommendation engine 416 may send a status that a consumable item will expire a predetermined amount of time prior to the expiration date of the consumable item. The predetermined period of time may be one or more days prior to the expiration date, one or more weeks prior to the expiration date, etc. This preemptive action provides the user with time to utilize the consumable item that will expire so as not to allow the consumable item to go to waste. The system may monitor the expiration dates of available consumable items as compared to the current date.

Responsive to determining that one or more consumable items will expire within the predetermined time period, method 700 may continue to block 715. In block 715, the system may send instruction(s) specifying a warning status to the user's control panel 436, smart glasses 438, mobile device 440, smart refrigerator 442, and/or smart pantry 444 specifying which consumable items have been identified in block 710.

In block 720, the system may determine whether one or more consumable items are expired. The system, for example, may compare the expiration dates of the consumable items with the current date and determine that the expiration dates have passed. Responsive to determining that the consumable item(s) have expired, method 700 may continue to block 725. In block 725, the system may send instruction(s) specifying an alert status for expired consumable items to one or more devices of the user. Responsive to determining that the consumable item(s) have not expired, method 700 may end.

For example, in the event that the expiration date of the consumable item has passed and the consumable item has not been consumed, used, or otherwise removed from the household (e.g., removed from smart refrigerator 442 and/or smart pantry 444), recommendation engine 416 may provide instructions specifying an alert status to a device of the user. In one exemplary implementation, recommendation engine 416 may cause smart glasses 438 to flash red responsive to the user picking up the expired consumable item. The expiration detection examples described may be used for food, medications, vitamins, and the like. Expiration detection may prevent a user from inadvertently ingesting an expired medication particularly during a time of distress or emergency.

In the above examples, the expiration date may be detected from a label of the consumable item or obtained from a merchant responsive to the user's purchase of the consumable item. In another arrangement, image processing may be used in cases where the consumable item does not specify an expiration date and no expiration date may have been obtained from the point of sale.

FIG. 8 is a flow chart illustrating another exemplary method 800 of expiration status detection. Method 800 may be performed by a data processing system (system) utilizing the architecture described with reference to FIG. 4.

In block 805, the system may obtain an image of a consumable item. In block 810, the system may identify the consumable item within the image, e.g., the particular type or kind of consumable item. In block 815, the system may obtain a reference image of the consumable item. The reference image is one that displays an unexpired, or healthy specimen, of the consumable item. In block 820, the system may compare the image of the consumable item with the reference image.

In block 825, the system may determine whether the consumable item is expired according to the comparison in block 820. In one aspect, image analytics 412 may determine features of the consumable item within the image such as coloration, markings, and the like, and compare the identified features with the same features determined from the reference image. In still another example, rather than use a reference image, the system may store one or more features characteristic of an unexpired version of the consumable item as opposed to a reference image. For instance, the system may store features extracted from an image of an unexpired version of the consumable item. The features determined from the image obtained in real time may be compared with the known features of the unexpired version of the consumable item. If the features match, the consumable item may be determined to have an unexpired status. If the features do not match, the consumable item may be determined to have an expired status.

Responsive to determining that the consumable item is expired, method 800 may continue to block 830. In block 830, the system may send a status indicating that the consumable item is expired. Responsive to determining that the consumable item is not expired, method 800 may continue to block 835. In block 835, the system may optionally send a status indicating that consumable item is not expired.

For purposes of illustration, consider the following example. Responsive to a user picking up a consumable item, e.g., a fruit or vegetable, a device of the user, e.g., smart glasses 438, may capture an image of the consumable item. Oral consumption analyzer 414 may determine the particular type of consumable item in the image, e.g., a tomato. Image analytics 412 may compare the image of the consumable item with a reference image of the consumable item or known features of an unexpired version of the consumable item. In another example, image analytics 412 may apply image correlation between the captured image of the consumable item and the reference image.

Based upon a comparison of the features of the captured image of the consumable item with the features of a known unexpired version of the consumable item, image analytics 412 may determine whether the consumable item is expired.

While the feature comparison described uses features of a known unexpired version of the consumable item, in another aspect, the system may store features that indicate expiration, e.g., spoilage. In that case, the detection of features, e.g., the matching of features, in the consumable item known to indicate expiration cause the system to determine that the consumable item has an expired status. In any case, recommendation engine 416 may send instructions to the user device indicating the status as to whether the consumable item is expired according to the comparison performed by image analytics 412.

Allergy Detection and Prevention

Figures 9, 10:
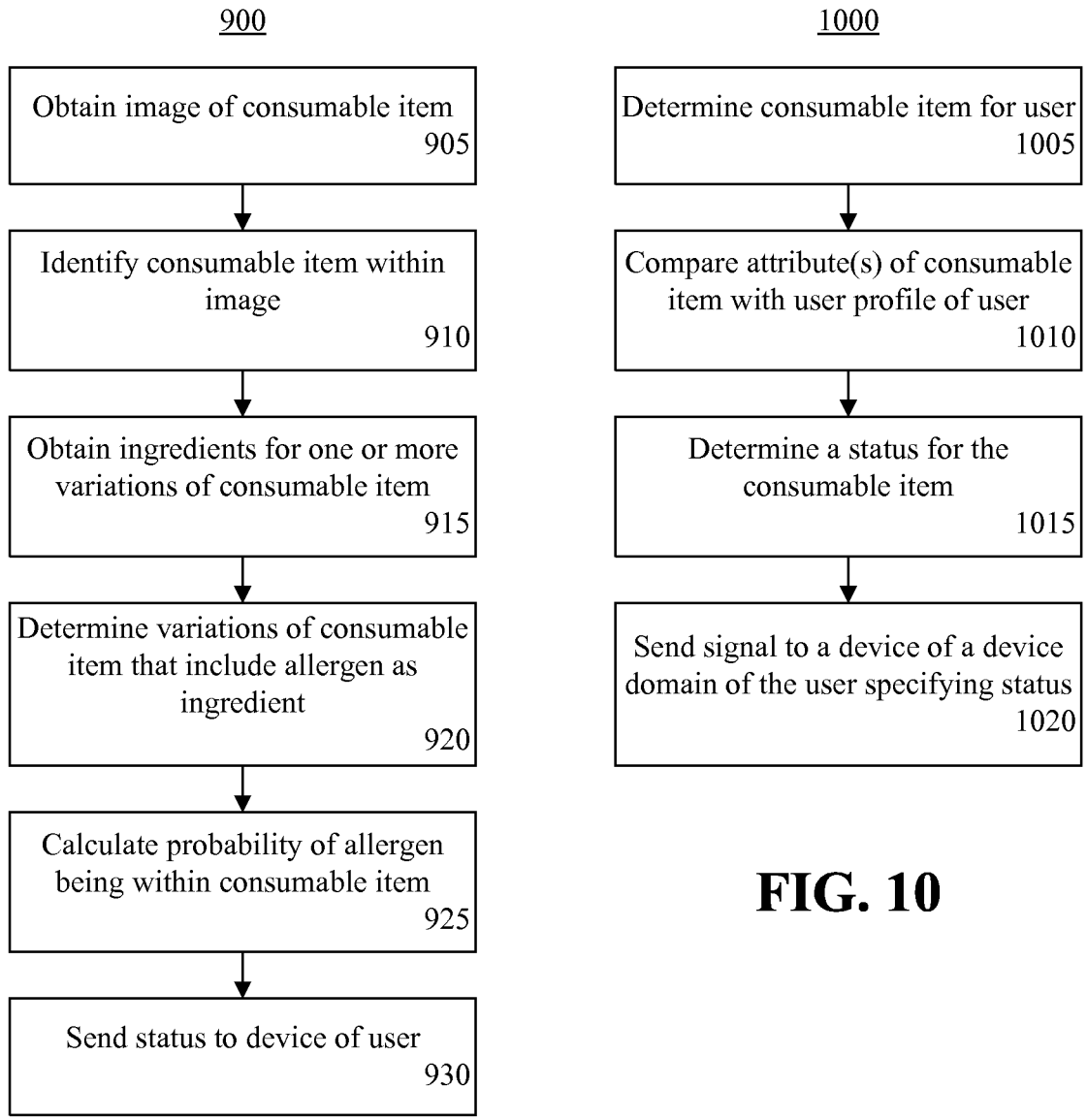
FIG. 9 is a flow chart illustrating an exemplary method of allergy status detection and prevention.
FIG. 10 is a flow chart illustrating an exemplary method of status detection for consumable items.

FIG. 9 is a flow chart illustrating an exemplary method 900 of allergy status detection and prevention. Method 900 may be performed by a data processing system (system) utilizing the architecture described with reference to FIG. 4. Method 900 illustrates how architecture 400 may be used to detect likely allergens and help a user to avoid the allergens.

In block 905, the system may obtain an image of a consumable item. The consumable item may be a meal or be a plurality of different food items. For example, a device such as smart glasses 438 may be used to obtain a picture of a meal, packaged food, or other item that may be consumed by a user. In block 910, the consumable item may be identified within the image. For example, image analytics 412 may determine the particular consumable item, e.g., different foods, in the image.

In block 915, the system may obtain a list of ingredients for one or more different variations, e.g., recipes, of the consumable item. In one aspect, community IOT concentrator 406 may communicate with enterprise IOT concentrator 420 to obtain a list of likely ingredients of the identified food. For example, nutritional fact finder 430 may query one or more databases 432 or other information sources for recipes for the identified consumable item. As an example, if the consumable food item is identified as apple pie, a plurality of apple pie recipes may be obtained, where each recipe includes an ingredient list.

In block 920, the system may determine the variations of the consumable item that include an allergen as an ingredient. For example, the system may search the ingredients of the retrieved recipes for allergens previously specified by the user and obtained from the user's profile. The system may compare the ingredients with the known allergens of the user from his or her profile.

In block 925, the system may calculate a probability of the allergen being within the consumable item. For example, nutritional fact finder 430 may determine, e.g., using a probabilistic data processing technique, whether the identified consumable item in the image poses an allergic threat to the user. In illustration, if the user has an allergy to peanuts, the system may determine that there is an 80% chance that the consumable item identified in the image includes peanut oil based upon the found recipes. As an example, 8 out of 10 recipes for the identified consumable item may have included peanut oil as an ingredient.

In block 930, the system may send instructions specifying a status to a device of the user. For example, recommendation engine 416 may send instructions that, when executed, cause the device to indicate a status specifying the likelihood of the food containing the identified allergen.

The example illustrated in FIG. 9 may be beneficial in cases where the user did not prepare the food that is to be consumed and, as such, is unaware of the ingredients. In still other arrangements, the system may identify a particular consumable item at the time of purchase as one that includes an allergen, e.g., by recognizing the packaging of the consumable item or a product code in an image, consulting nutritional fact finder 430, which may query database 432, and comparing retrieved nutritional data, which may include ingredients, with the allergens in the user profile.

Medication Monitoring

In one arrangement, individuals such as physicians, pharmacists, care providers, and users (patients) may provide information such as prescribed medications, dosage, times of medication consumption, medication requirements, and medication side effects through control panel 436. In another arrangement, the medication information may be read from pharmaceutical database 452, for example, as shared through global IOT community 404 via IOT integration services 428. In still another arrangement, a device of the user (e.g., smart glasses 438, mobile device 440, a health monitor, etc.) may be used to scan or obtain an image of the label of the medication to obtain the oral intake instructions. The oral intake instructions may be stored in the user profile within database 432 or device data 408 in association with the medication.

One or more of the devices of the user's device domain may monitor to determine whether the user picks up the medication. Responsive to the user picking up the medication, the system may retrieve the oral intake instructions from database 408. Devices such as smart glasses 438, personal fitness/health monitoring devices, intelligent kitchen appliances, and smart devices such as intelligent prescription containers may operate cooperatively and send data to community IOT concentrator 406 to be stored in device data 408. Personal pattern recognition engine 410 may analyze device data 408 and may regulate when and what medications and/or other food items have been consumed by the user.

In one aspect, the aggregation of medical information may be compared with the information and/or requirements specified by the user to develop personal user patterns. For example, personal pattern recognition engine 410 may receive the medical information for a user and the user's nutritional, medical, and/or other objectives. Personal pattern recognition engine 410 may send instructions specifying statuses to one or more devices of the user responsive to a user attempting to consume medicine that the user has already consumed. For example, the system may send instructions to a smart watch to display an alert status or send instructions to a prescription container to lock, e.g., when determined to have a status of unlocked.

As an illustrative example, consider the case where a user is supposed to take a medication two times per day for one week. Each day, the user is to take a first dose followed by a second dose two hours later without consuming food between the two doses. Recommendation engine 416 may send an alert to one or more of the user devices to consume a first dose (e.g., a pill). If the user picks up or touches an item identified as a food item within the two hour time period following consumption of the first dose, recommendation system 416 may send a warning or alert status. Responsive to detecting that two hours have passed since consuming the first dose, recommendation engine 416 may send a status to the user's device instructing the user take the second dose. The restriction against consuming food may be removed responsive to determining that the second dose has been consumed.

In another aspect, a medication dispenser may be one of the devices within the user's device domain. In that case, recommendation engine 416 may send instructions to the medication dispenser to unlock responsive to determining that the time for the user to take a medication has occurred.

For example, the system may determine that the status of the medications is now "consume" thereby causing the system to end unlock instructions. Referring to the above example, the medication dispenser may remain locked, responsive to lock instructions from the system, until two hours from the user taking the first dose have passed. At or about two hours after detecting the user taking the first dose, the system may send instructions to unlock to the medical dispenser thereby allowing the user to obtain the second dose of medication. The instructions provided may depend upon the status of the receiving device. For example, the system may determine that the medical dispenser has a locked status prior to sending an instruction to unlock. Similarly, the system may determine that the medical dispenser has an unlocked status prior to sending an instruction to lock. As previously discussed, the locking and/or unlocking of a device may be used with other smart appliances to limit or otherwise regulate food consumption.

In yet another illustrative example, a physician of the user may enter a medication that must be consumed by the user each day with food. Personal pattern recognition engine 410, smart glasses 438, and control panel 436 may operate cooperatively to ensure that the user meets the requirements. For example, smart glasses 438 in combination with personal pattern recognition engine 410 may determine that the user has consumed food in the morning. Data from personal pattern recognition engine 410 may be provided to recommendation engine 416. Responsive to recommendation engine 416 receiving the confirmed data from personal pattern recognition engine 410 that the user has consumed food, recommendation engine 416 may send an unlock status to a medication dispenser thereby causing the medication dispenser to unlock.

By comparison, if recommendation engine 416 receives information that is indicative that the user should not consume the medication, e.g., abnormally high blood pressure from a health monitor, or the like, despite consuming food, recommendation engine 416 may continue to keep the medication dispenser locked. Further, recommendation engine 416 may send a message to a device of the physician of the user.

In another example, an elderly user may have a caregiver registered with the system. The elderly user may be afflicted with Alzheimer's disease or other condition that may prevent the user from recalling consumed medications, dosages, and/or even the consumption of a meal. The elderly user may wear smart glasses thereby allowing the system to track consumption of medication, food, and determine dosages (amounts) consumed, and which meals have been taken. The system may send instructions to a device of the caregiver specifying status information. The status information may indicate that the elderly user being cared for has properly consumed medication scheduled for morning consumption, had breakfast, etc. In one arrangement, the system may send an image of the meal or other items consumed for informational purposes.

Referring to the prior example, the elderly user may reside at a day care facility. The system allows a caregiver to monitor the activities of the elderly user. For example, if a medication is not provided to the elderly user after a certain time period, the system may notify the caregiver. The caregiver may contact the day care facility to check on the elderly user to ensure that proper procedures relating to nutrition and/or medication are being followed.

Consider another example where the smart appliance is a medication dispenser. A user may visit a pharmacy to refill a prescription. The user may not recall the prescription. The user may use a smart phone or smart glasses to query the medication dispenser for the name of the medication and/or quantity of medication left. The information may then be shared with the pharmacist, for example, through global IOT dashboard 434.

Personal Pattern Recognition Examples

In another arrangement, personal pattern recognition engine 410 may operate with devices of the user's device domain including the various health monitors previously mentioned to obtain biometric data for the user. In one aspect, personal pattern recognition engine 410 may be a device data aggregation and processor. In illustration, personal pattern recognition engine 410 may log when a user consumed a certain food or medication. Personal pattern recognition engine 410 may log biometric data including, but not limited to, body temperature, blood pressure, physical activity, hours slept, heartrate at rest, heartrate when active, and the like.

In one aspect, personal pattern recognition engine 410 may aggregate the biometric data with the consumption data. Personal pattern recognition engine 410 may determine correlations between historical oral intake information, e.g., consumable items consumed by the user, and one or more trends in the biometric data. For example, personal pattern recognition engine 410 may accurately track side effects experienced by a user that may be accurately correlated, e.g., using date and time stamps, with the consumption of medication.

In another example, personal pattern recognition engine 410 may utilize analytics to make associations and recommendations for the user automatically. As discussed, architecture 400 may include historical oral intake information and correlated biometric data. Using smart glasses 438, for example, personal pattern recognition engine 410 may determine that within a predetermined amount of time after consuming a particular food item or a particular brand of a particular food item, the user exhibits signs of fatigue. As an example, smart glasses 438, which may include retinal scanners, may detect slower eyeball reactions and/or the closing of the user's eyelids (e.g., with greater frequency, of greater duration, etc.). If the user consumes the particular brand of the food item weekly and personal pattern recognition engine 410 detects this pattern or trend, recommendation engine 416 may send instructions to a device of the user notifying the user of the observed trend such as "you exhibit signs of fatigue after eating consumable item X".

Personal pattern recognition engine 410 may analyze consumption data as may be obtained from the smart pantry, smart refrigerator, smart glasses, etc., along with nutritional data correlated with consumed items. Personal pattern recognition engine 410 may analyze the aforementioned data in combination with data from devices such as blood pressure monitors and/or activity monitors to determine how consumption influences health indicators such as fatigue. In another example, the system may determine that a user consumed an excess amount of calories on a particular day. The system may suggest a modification to a user's daily activity goal that may be monitored by the system. In illustration, the system may adjust an activity related objective or goal of the user by increasing the number of steps to take in a day. The system may raise the user's objective from 10,000 steps to 12,500 steps, for example.

FIG. 10 is a flow chart illustrating an exemplary method 1000 of status detection for consumable items. Method 1000 may be performed by a data processing system (system) executing architecture 400.

In block 1005, the system may determine a consumable item for a user. The system may determine a consumable item using any of the various devices of a device domain as described herein. In block 1010, the system may compare attributes of the consumable item determined in block 1005 with the user profile of the user. As discussed, attributes of the consumable item may include nutritional data including ingredients, oral intake instructions, medical information such as medication interactions and the like. The user profile may specify objectives, allergens, other prescribed medications, and the like.

In block 1015, the system may determine a status for the consumable item. The status may be expired, unexpired, recommended, not recommended, or the like. The status may be determined through the comparison in block 1010. A consumable item having a known allergen, for example, will have a "not recommended" status. A consumable item determined to be inconsistent with the objectives of the user profile also may have a status of "not recommended." In block 1020, the system may send instruction(s) to one or more devices of the device domain of the user specifying the status.

Figure 11:
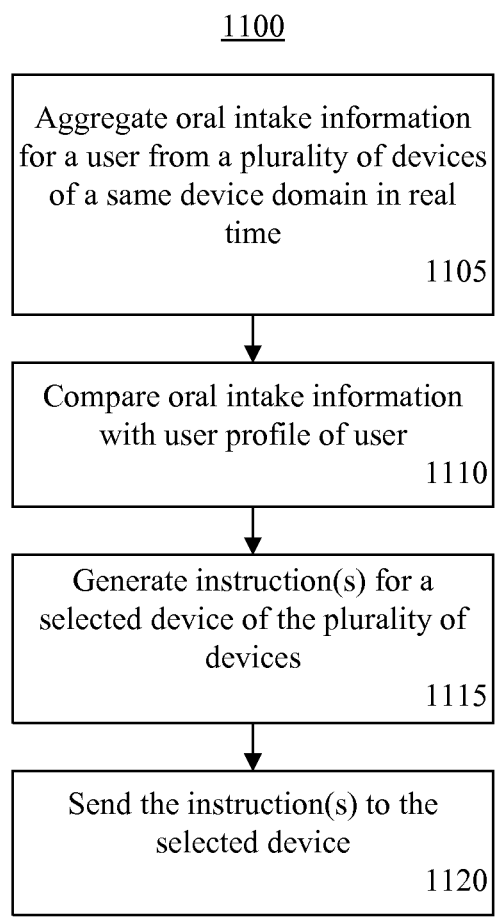
FIG. 11 is a flow chart illustrating an exemplary method of monitoring oral intake for consumable items.

FIG. 11 is a flow chart illustrating an exemplary method 1100 of monitoring oral intake of consumable items. Method 1100 may be performed by a data processing system (system) executing architecture 400.

In block 1105, the system may aggregate oral intake information for a user from a plurality of devices belonging to a same device domain of the user. The oral intake information may be aggregated in real time. Aggregating oral intake information may include receiving oral intake information from a plurality of devices of a device domain and storing the information in a data store. Aggregating the oral intake information may include receiving unprocessed data such as images and extracting data from the images such as identified consumable items, amount consumed, obtaining nutritional data for consumable items, consumable items and/or attributes thereof, and the like.

In block 1110, the system may compare the oral intake information with information within the user profile of the user. The system may compare the oral intake information with objectives, medical information including prescriptions and/or allergens, or the like. In block 1115, the system may generate one or more instructions for a selected device of the plurality of devices according to the comparing. The instruction(s), when executed by the selected device, may cause the selected device to initiate one or more executable operations. For example, the selected device may provide a recommendation specified by the instruction(s), provide one or more statuses, change operating state such as lock and/or unlock, or the like. In block 1120, the system may send the instruction(s) to the selected device. The selected device may execute the instruction(s).

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

For purposes of explanation, specific nomenclature is set forth to provide a thorough understanding of the various inventive concepts disclosed herein. The terminology used herein, however, is for the purpose of describing particular aspects of the inventive arrangements only and is not intended to be limiting.

As defined herein, the singular forms "a," "an," and "the" are intended to include the plural forms as well, unless the context clearly indicates otherwise. As defined herein, the term "another" means at least a second or more. As defined herein, the terms "at least one," "one or more," and "and/or," are open-ended expressions that are both conjunctive and disjunctive in operation unless explicitly stated otherwise. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. As defined herein, the term "automatically" means without user intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. Memory elements, as described herein, are examples of a computer readable storage medium. A non-exhaustive list of more specific examples of a computer readable storage medium may include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing.

As defined herein, the term "coupled" means connected, whether directly without any intervening elements or indirectly with one or more intervening elements, unless otherwise indicated. Two elements may be coupled mechanically, electrically, or communicatively linked through a communication channel, pathway, network, or system. As defined herein, the terms "includes," "including," "comprises," and/or "comprising," specify the presence of stated features, integers, steps, operations, elements, and/or components, but do not preclude the presence or addition of one or more other features, integers, steps, operations, elements, components, and/or groups thereof. As defined herein, the term "output" means storing in physical memory elements, e.g., devices, writing to display or other peripheral output device, sending or transmitting to another system, exporting, or the like. As defined herein, the term "plurality" means two or more than two.

As defined herein, the term "executable operation" is a task performed by a data processing system or a processor within a data processing system unless the context indicates otherwise. Examples of executable operations include, but are not limited to, "processing," "computing," "calculating," "determining," "displaying," "comparing," or the like. In this regard, operations refer to actions and/or processes of the data processing system, e.g., a computer system, or similar electronic computing device, that manipulates and transforms data represented as physical (electronic) quantities within the computer system's registers and/or memories into other data similarly represented as physical quantities within the computer system memories and/or registers or other such information storage, transmission or display devices.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context. As defined herein, the term "responsive to" means responding or reacting readily to an action or event. Thus, if a second action is performed "responsive to" a first action, there is a causal relationship between an occurrence of the first action and an occurrence of the second action. The term "responsive to" indicates the causal relationship.

As defined herein, the term "processor" means at least one hardware circuit configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "real time" means a level of processing responsiveness that a user or system senses as sufficiently immediate for a particular process or determination to be made, or that enables the processor to keep up with some external process. As defined herein, the term "user" means a human being. The terms first, second, etc. may be used herein to describe various elements. These elements should not be limited by these terms, as these terms are only used to distinguish one element from another unless stated otherwise or the context clearly indicates otherwise.

Reference throughout this disclosure to "one embodiment," "an embodiment," or similar language means that a particular feature, structure, or characteristic described in connection with the embodiment is included in at least one embodiment described within this disclosure. Thus, appearances of the phrases "in one embodiment," "in an embodiment," and similar language throughout this disclosure may, but do not necessarily, all refer to the same embodiment.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of monitoring oral intake of consumable items, comprising:
   aggregating, using a processor, oral intake information for a user from a plurality of devices belonging to a same device domain of the user in real time;
   comparing, using the processor, the oral intake information with a user profile of the user;
   generating, using the processor, an instruction for a selected device of the plurality of devices according to the comparing; and
   sending, using the processor, the instruction to the selected device, wherein
   the selected device is smart glasses that executes the instruction and are configured to display information,
   the comparing the oral intake information comprises:
      retrieving ingredients for each of a plurality of variations of a detected consumable item;
      comparing an allergen of the user from the user profile with the ingredients of the plurality of variations of the consumable item; and
      determining a probability of the consumable item including the allergen based upon the retrieved ingredients of the plurality of variations of the consumable item,
   results in a determination that the consumable item is expired, and
   the instruction, upon the determination that the consumable item is expired, is to display, within the smart glasses, a visual indication that consumable item is expired, wherein
   the detected consumable items is determined from image data generated by at least one of the plurality of devices.

2. The method of claim 1, further comprising:
determining a status of the selected device of the device domain;
wherein the instruction is also generated according to the status of the selected device.

3. The method of claim 1, wherein
the oral intake information specifies a plurality of available consumable items, the method further comprising:
detecting removal of a consumable item from an appliance device of the device domain; and
marking the consumable item as unavailable responsive to the detecting.

4. The method of claim 1, further comprising:
correlating consumption data with biometric data for the user;
detecting a user pattern from the correlated consumption data and biometric data; and
sending a further instruction, determined according to the biometric data for the user pattern, to the selected device of the device domain.

5. The method of claim 1, wherein
comparing the oral intake information comprises:
comparing a visual feature of a consumable item with a reference visual feature; and
determining whether the consumable item is expired according to the comparing of the visual feature with the reference visual feature.

6. The method of claim 1, wherein
comparing the oral intake information comprises:
comparing an expiration date of a consumable item with a current date; and
determining whether the consumable item is expired or is to expire within a predetermined amount of time.

7. A system for monitoring oral intake of consumable items, comprising:
a processor programmed to initiate executable operations comprising:
   aggregating oral intake information for a user from a plurality of devices belonging to a same device domain of the user in real time;
   comparing the oral intake information with a user profile of the user;
   generating an instruction for a selected device of the plurality of devices according to the comparing; and
   sending the instruction to the selected device, wherein
the selected device is smart glasses that executes the instruction and are configured to display information,
the comparing the oral intake information comprises:
   retrieving ingredients for each of a plurality of variations of a detected consumable item;
   comparing an allergen of the user from the user profile with the ingredients of the plurality of variations of the consumable item; and determining a probability of the consumable item including the allergen based upon the retrieved ingredients of the plurality of variations of the consumable item, results in a determination that the consumable item is expired, and the instruction, upon the determination that the consumable item is expired, is to display, within the smart glasses, a visual indication that consumable item is expired, wherein the detected consumable items is determined from image data generated by at least one of the plurality of devices.

8. The system of claim 7, wherein
the processor is further programmed to initiate executable operations comprising:
determining a status of the selected device of the device domain;
wherein the instruction is also generated according to the status of the selected device.

9. The system of claim 7, wherein
the oral intake information specifies a plurality of available consumable items, and wherein the processor is further programmed to initiate executable operations comprising:
detecting removal of a consumable item from an appliance device of the device domain; and
marking the consumable item as unavailable responsive to the detecting.

10. The system claim 7, wherein
the processor is further programmed to initiate executable operations comprising:
correlating consumption data with biometric data for the user;
detecting a user pattern from the correlated consumption data and biometric data; and
sending a further instruction, determined according to the biometric data for the user pattern, to the selected device of the device domain.

11. The system of claim 7, wherein
comparing the oral intake information comprises:
comparing a visual feature of a consumable item with a reference visual feature; and
determining whether the consumable item is expired according to the comparing of the visual feature with the reference visual feature.

12. The system of claim 7, wherein
comparing the oral intake information comprises:
comparing an expiration date of a consumable item with a current date; and
determining whether the consumable item is expired or is to expire within a predetermined amount of time.

13. A computer program product, comprising
a computer readable storage medium having program code stored thereon for monitoring oral intake of consumable items,
the program code executable by a processor to perform:
aggregating oral intake information for a user from a plurality of devices belonging to a same device domain of the user in real time;
comparing the oral intake information with a user profile of the user;
generating an instruction for a selected device of the plurality of devices according to the comparing; and
sending the instruction to the selected device, wherein
the selected device is smart glasses that executes the instruction and are configured to display information,
the comparing the oral intake information comprises:
retrieving ingredients for each of a plurality of variations of a detected consumable item;
comparing an allergen of the user from the user profile with the ingredients of the plurality of variations of the consumable item; and
determining a probability of the consumable item including the allergen based upon the retrieved ingredients of the plurality of variations of the consumable item,
results in a determination that the consumable item is expired, and
the instruction, upon the determination that the consumable item is expired, is to display, within the smart glasses, a visual indication that consumable item is expired, wherein
the detected consumable items is determined from image data generated by at least one of the plurality of devices.

14. The computer program product of claim 13, wherein
the method further comprises:
determining a status of the selected device of the device domain;
wherein the instruction is also generated according to the status of the selected device.

15. The computer program product of claim 13, wherein
the oral intake information specifies a plurality of available consumable items, the method further comprising:
detecting removal of a consumable item from an appliance device of the device domain; and
marking the consumable item as unavailable responsive to the detecting.

16. The computer program product of claim 13, further comprising:
correlating consumption data with biometric data for the user;
detecting a user pattern from the correlated consumption data and biometric data; and
sending a further instruction, determined according to the biometric data for the user pattern, to the selected device of the device domain.

17. The computer program product of claim 13, wherein
comparing the oral intake information comprises:
comparing a visual feature of a consumable item with a reference visual feature; and
determining whether the consumable item is expired according to the comparing of the visual feature with the reference visual feature.

18. The computer program product of claim 13, wherein
comparing the oral intake information comprises:
comparing an expiration date of a consumable item with a current date; and
determining whether the consumable item is expired or is to expire within a predetermined amount of time, wherein
the instruction specifies the status.

* * * * *